(12) United States Patent
Sepello et al.

(10) Patent No.: US 12,343,240 B2
(45) Date of Patent: Jul. 1, 2025

(54) DURABLE ABSORBENT PANT

(71) Applicant: The Procter & Gamble Company, Cincinnati, OH (US)

(72) Inventors: Cassandra A. Sepello, Loveland, OH (US); Ashley Basius, Cincinnati, OH (US); Bret D. Seitz, West Chester, OH (US); Roi Kurt Ballin, Hoboken, NJ (US); Amit Ron Ronkin, Ramot Hashavim (IL)

(73) Assignee: The Procter & Gamble Company, Cincinnati, OH (US)

( * ) Notice: Subject to any disclaimer, the term of this patent is extended or adjusted under 35 U.S.C. 154(b) by 240 days.

(21) Appl. No.: 17/159,462

(22) Filed: Jan. 27, 2021

(65) Prior Publication Data

US 2021/0290447 A1 Sep. 23, 2021

Related U.S. Application Data

(60) Provisional application No. 62/966,142, filed on Jan. 27, 2020.

(51) Int. Cl.
*A61F 13/15* (2006.01)
*A61F 13/496* (2006.01)
*A61F 13/511* (2006.01)

(52) U.S. Cl.
CPC ...... *A61F 13/15203* (2013.01); *A61F 13/496* (2013.01); *A61F 13/51121* (2013.01); *A61F 2013/51139* (2013.01)

(58) Field of Classification Search
CPC .............. A61F 13/15203; A61F 13/496; A61F 13/51121; A61F 2013/51139;
(Continued)

(56) References Cited

U.S. PATENT DOCUMENTS 2,705,957 A     4/1955  Virginia
3,909,851 A  *  10/1975 Garrou ................... A41B 11/14
                                                          2/409

(Continued)

FOREIGN PATENT DOCUMENTS

CA      2255465 A1    6/2000
CA      2827795 A1    11/2013
(Continued)

OTHER PUBLICATIONS

PCT Search Report and Written Opinion for PCT/US2021/070080 dated May 18, 2021, 13 pgs.
(Continued)

*Primary Examiner* — Rebecca E Eisenberg
*Assistant Examiner* — Katherine-Ph Minh Pham
(74) *Attorney, Agent, or Firm* — Sarah M. DeCristofaro

(57) ABSTRACT

A durable absorbent pant is disclosed. The pant includes a crotch portion with a crotch gusset including an absorbent assembly. The crotch gusset may be configured to exhibit a maximum Longitudinal Elongation of 25 percent to 100 percent and a Longitudinal Tensile Modulus of 10 gf/mm to 100 gf/mm. The described stretch characteristics provide a pant with improved body conformity for improved containment of fluids (such as urine) discharged by the wearer.

17 Claims, 8 Drawing Sheets

(58) Field of Classification Search
CPC ...... A61F 13/15268; A61F 2013/15276; A61F 2013/15373; A61F 2013/15463
See application file for complete search history.

(56) References Cited

U.S. PATENT DOCUMENTS

| | | | |
|---|---|---|---|
| 4,355,425 A | 10/1982 | Jones et al. | |
| 5,085,653 A * | 2/1992 | Levy | A61F 13/49003 604/383 |
| 5,248,309 A * | 9/1993 | Serbiak | A61F 13/511 604/374 |
| 5,562,648 A * | 10/1996 | Peterson | A61F 13/496 604/393 |
| 5,851,204 A | 12/1998 | Mizutani | |
| 6,258,455 B1 * | 7/2001 | Clarke | A61L 2/16 428/394 |
| 6,393,621 B1 | 5/2002 | Redwine et al. | |
| 6,884,494 B1 * | 4/2005 | Curro | A47L 13/17 428/196 |
| 7,118,639 B2 * | 10/2006 | DeLucia | B32B 37/144 156/244.11 |
| 7,322,966 B1 | 1/2008 | Deerin | |
| 7,458,961 B2 | 12/2008 | Carstens | |
| 7,462,173 B2 * | 12/2008 | Carstens | A61F 13/15203 604/385.01 |
| 7,846,145 B2 | 12/2010 | Carstens | |
| 8,099,794 B2 | 1/2012 | Carstens | |
| 8,117,675 B2 | 2/2012 | Strange et al. | |
| 8,262,638 B2 | 9/2012 | Carstens | |
| 8,348,918 B2 | 1/2013 | Carstens | |
| 8,454,570 B2 | 6/2013 | Carstens | |
| 8,679,085 B2 | 3/2014 | Ronstroem | |
| 8,998,870 B2 | 4/2015 | Roe | |
| 9,980,861 B2 | 5/2018 | Deerin | |
| 10,441,480 B2 | 10/2019 | Griffiths | |
| 11,154,431 B1 | 10/2021 | Yip et al. | |
| 11,207,225 B2 | 12/2021 | Kajanthan | |
| 11,395,774 B2 | 7/2022 | Skinner | |
| 2002/0004349 A1 * | 1/2002 | Tsujiyama | A61F 13/51401 442/381 |
| 2002/0016580 A1 | 2/2002 | Wada | |
| 2003/0097109 A1 | 5/2003 | Bruce | |
| 2005/0120466 A1 | 6/2005 | Coenen et al. | |
| 2005/0142331 A1 | 6/2005 | Anderson | |
| 2005/0229293 A1 | 10/2005 | Miller | |
| 2006/0070163 A1 * | 4/2006 | Beck | A41D 27/12 2/69 |
| 2006/0264869 A1 | 11/2006 | Carstens | |
| 2006/0264883 A1 | 11/2006 | Carstens | |
| 2006/0264884 A1 | 11/2006 | Carstens | |
| 2007/0012519 A1 | 1/2007 | Angielski | |
| 2007/0106354 A1 | 5/2007 | Carstens | |
| 2008/0147031 A1 | 6/2008 | Long et al. | |
| 2010/0249736 A1 * | 9/2010 | Png | A41B 17/00 604/378 |
| 2011/0172621 A1 | 7/2011 | Lee | |
| 2013/0226120 A1 * | 8/2013 | Van De Maele | B32B 29/005 428/206 |
| 2014/0018763 A1 | 1/2014 | Evenson et al. | |
| 2014/0039432 A1 | 2/2014 | Dunbar et al. | |
| 2014/0257228 A1 | 9/2014 | Wang et al. | |
| 2014/0257229 A1 | 9/2014 | Wang et al. | |
| 2016/0089276 A1 | 3/2016 | Griffiths | |
| 2016/0100997 A1 | 4/2016 | Seitz | |
| 2016/0166447 A1 | 6/2016 | Toro | |
| 2016/0184146 A1 | 6/2016 | Tulk | |
| 2020/0000155 A1 | 1/2020 | Etienne | |
| 2021/0030605 A1 | 2/2021 | Kajanthan et al. | |
| 2021/0100698 A1 | 4/2021 | Langdon et al. | |
| 2022/0354710 A1 | 11/2022 | Sepello et al. | |
| 2023/0157375 A1 | 5/2023 | Seitz | |
| 2024/0000622 A1 | 1/2024 | Stanley et al. | |
| 2024/0050288 A1 | 2/2024 | Basius | |
| 2024/0065901 A1 | 2/2024 | Stanley | |

FOREIGN PATENT DOCUMENTS

| | | |
|---|---|---|
| CN | 1313745 A | 9/2001 |
| CN | 1897834 A | 1/2007 |
| CN | 101027022 A | 8/2007 |
| CN | 101926709 A | 12/2010 |
| CN | 104203182 A | 12/2014 |
| CN | 110022817 A | 7/2019 |
| EP | 0811362 A1 | 12/1997 |
| EP | 1166738 A2 | 1/2002 |
| EP | 1 370 161 | 5/2006 |
| EP | 2 412 353 | 4/2015 |
| EP | 2968030 B1 | 4/2018 |
| JP | 4266604 B2 | 2/2009 |
| KR | 10-0694187 | 3/2007 |
| WO | 2004004619 A1 | 1/2004 |
| WO | 2013186577 A1 | 12/2013 |
| WO | 2015156686 A2 | 10/2015 |
| WO | 2021155397 A1 | 8/2021 |
| WO | 2022235734 A1 | 11/2022 |

OTHER PUBLICATIONS

All Office Actions; U.S. Appl. No. 18/645,742, filed Apr. 25, 2024.

Anonymous, "Femtis—Perioden Panties—Periodenslip ELLA", XP093016146, Retrieved from the Internet: URL: https://web.archive.org/web/20210726170425/https://www.femtis.de/periodenslips/perioden-slip-ella-rot.html [retrieved on Jan. 20, 2023], Jul. 26, 2021, 9 pages.

Anonymous, "Inkontinenzslip: hydas.de", XP093016138, Retrieved from the Internet: URL: https://web.archive.org/web/20210412055014/https://www.hydas.de/inkontinenzslip [retrieved on Jan. 20, 2023], Apr. 12, 2021, 57 pages.

Anonymous, "Periodenpantys 2er-Pack Spitze schwarz—Secret Care", XP093016049, Retrieved from the Internet: URL: https://web.archive.org/web/20210415173928/https://www.schiesser.com/damenbekleidung-unterwaesche-slips-pants-periodenpantys-2er-pack-spitze-schwarz-secret-care.html [retrieved on Jan. 20, 2023], Apr. 15, 2021, 19 pages.

Unpublished U.S. Appl. No. 18/645,742, filed Apr. 25, 2024, to Jill Marlene Orr et al.

* cited by examiner

DURABLE ABSORBENT PANT

CROSS REFERENCE TO RELATED APPLICATION

To the extent appropriate this application claims the benefit of U.S. Provisional Application No. 62/966,142, filed Jan. 27, 2020, the substance of which is incorporated herein by reference.

FIELD OF THE INVENTION

This invention relates to features of durable absorbent pants (for example, underwear briefs) to be worn for containing and absorbing discharges resulting from urinary incontinence and/or menstruation.

BACKGROUND

In recent years populations in many developed countries have shifted toward middle-aged and older demographic groups. These demographic groups represent markets with relatively increased demands for products addressed to concerns associated with aging.

One such concern is adult urinary incontinence. Urinary incontinence can result from or be exacerbated by a variety of health conditions, and for women, even normal experiences including childbearing or simply aging.

Disposable absorbent pants for adults experiencing urinary incontinence have been marketed for a number of years. These products have traditionally exhibited varying degrees of similarities in appearance, feel and bulkiness to disposable diapers or disposable children's training pants. Finding these similarities undesirable, many active people experiencing only mild to moderate incontinence have preferred not to use these products, opting to use durable/washable absorbent underwear, or durable ordinary underwear in combination with a disposable absorbent pad held in place by/within the underwear.

A problem presented in designing a system to be used to contain and absorb unintended small discharges of urine by a woman lies in the tendency of urine, exiting the body at relatively lower volume and velocity, to adhere and flow along skin surfaces and body contours (herein, "adhering flow"). Depending upon the woman's body position during an unintended discharge, adhering urine flow along external skin surfaces can find its way through gaps between the skin and containment features of the selected containment/absorbent system (e.g. underwear leg bands, cuffs and other containment features of absorbent underwear and/or pad), and thereby, escape capture by the absorbent portions of the system and soil surrounding portions of underwear, outer clothing, bedclothes, etc.

Currently available durable absorbent underwear pants do not sufficiently maintain contact with the wearer's body to reliably intercept adhering urine flow and direct it to absorbent components. There is an unsatisfied need for a durable underwear/absorbent system that provides and maintains effective contact with the wearer's body through ordinary wear and body movements, to more reliably contain and absorb unintended discharges of urine while being comfortable, discreet under clothing and esthetically pleasing to the wearer.

DEFINITIONS

Figure 1:
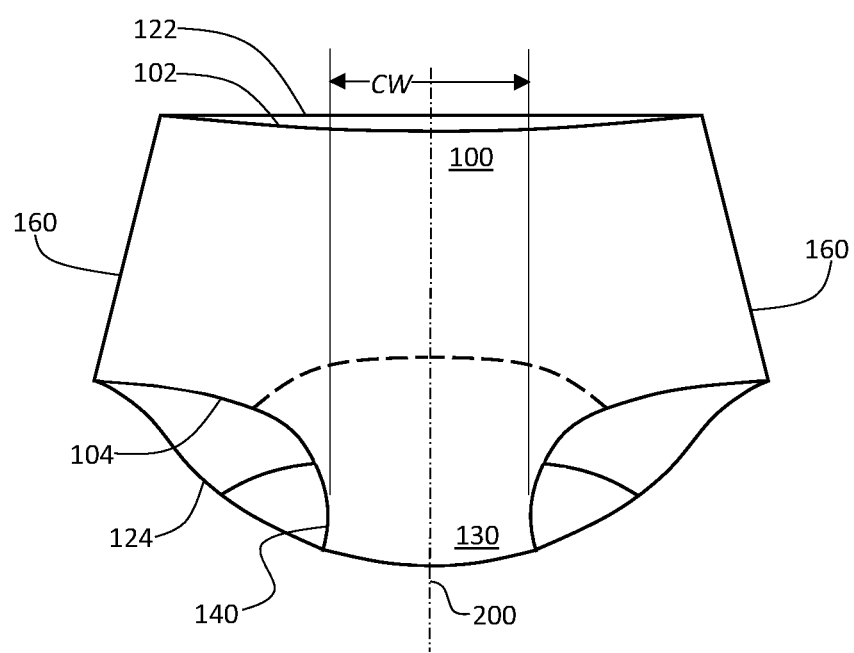
FIG. 1 is a simplified depiction of an example of a brief pant, as it would appear laid out flat on a horizontal planar surface, front waist portion facing up.

With respect to a wearable garment such as a pant, "durable" means made predominately of cloth material that is knitted and/or woven from natural, semi-synthetic or synthetic fiber, thread or yarn, and which may be normally laundered or hand-washed and dried for reuse/re-wear a plurality of times without substantial loss of original shape, structure or useful mechanical attributes.

With respect to a pant in an opened configuration, laid out flat on a horizontal planar surface, "longitudinal" refers to a direction generally perpendicular to a line tangent each of the left and right leg opening edges where they are closest the front waist edge. With respect to a pant in an assembled configuration, laid out flat on a horizontal planar surface, front waist portion facing up, "longitudinal" refers to a direction generally perpendicular to a line tangent each of the left and right leg opening edges where they are closest the front waist edge. "Length" refers to a dimension measured along the longitudinal direction.

With respect to a pant in an opened configuration, laid out flat on a horizontal planar surface, "lateral" refers to a direction generally parallel to a line tangent each of the left and right leg opening edges where they are closest the front waist edge. With respect to a pant in an assembled configuration, laid out flat on a horizontal planar surface, front waist portion facing up, "lateral" refers to a direction generally parallel to a line tangent each of the left and right leg opening edges where they are closest the front waist edge. "Width" refers to a dimension measured along the lateral direction.

With respect to a pant in an opened configuration, laid out flat on a horizontal planar surface, the "z-direction" is the direction orthogonal to the longitudinal and lateral directions, i.e., the vertical direction relative the horizontal planar surface.

With respect to respective layer components in a crotch gusset of a pant in an opened configuration, laid out flat on a horizontal planar surface, wearer-facing surfaces facing up, as between first and second layer components in the crotch portion, the terms "above," "superadjacent," "below," "subjacent" and/or "beneath" describe the components' disposition along the z-direction relative each other. Thus, for example, referring to FIG. 3C, a wearer-facing layer 131a is disposed "above" an outward-facing layer 131d, and conversely, the outward-facing layer 131d is disposed "below" the wearer-facing layer 131a and/or absorbent layer 131b. "Superadjacent" and "subjacent" with respect to two layer components, mean further that the two layer components are disposed in direct surface-to-surface contact with each other.

A yarn, thread, fiber, filament, web, film or fabric material, or a laminate or composite of any of these, is considered to be "elastic" or "elastomeric" for purposes herein if, when a tensile force no greater than 50 gf/mm (gf per mm of sample width, where width is measured perpendicular to the stretch direction) is applied to the subject material along a stretch direction, the material may be extended along the direction to an elongated dimension of at least 130% of its original relaxed dimension (i.e., can extend at least 30%), without rupture or breakage which substantially damages the subject material; and when the force is removed from the subject material, the material retracts along the stretch direction to recover at least 40% of such elongation. To illustrate, if a section of fabric having an original relaxed length of 100 mm and a width of 40 mm can be elongated by tensile force of 2000 gf (50 gf/mm) in a direction along its length to 130 mm length without substantial damage, and will retract upon removal of the force to a length no greater than 118 mm (130 mm-118 mm=12 mm=40% of 30 mm), it is "elastic" as defined herein. "Elongation," used herein to quantify and express an amount of strain imparted to an elastic material in a stretch direction, means: {[(strained length of the strand)−(length of the strand before straining)]/(length of the strand before straining)}, ×100%.

With respect to two opposing surfaces of a layer component of a pant, or combination of layer components, "wearer-facing" refers to the surface that faces the wearer's skin when the pant is worn normally; and "outward-facing" refers to the surface that faces away from the wearer's skin. With respect to two distinct layered components of a pant, the "wearer-facing" component is the component that is disposed closest the wearer's skin when the pant is worn normally; and the "outward-facing" component is the component that is disposed farthest from the wearer's skin.

For purposes herein, "pant" includes any garment adapted for wear about the human lower torso, including a front waist portion and a rear waist portion that join about the wearer's hips and beneath the wearer's crotch, to form a garment having a waist opening and a pair of leg openings. Herein, the term "pant" encompasses (but is not limited to) a garment defined herein as a "brief pant"; a garment defined herein as a "legged pant", and any other garment whether adapted for use as underwear or outerwear, having such features.

For purposes herein, unless otherwise specified, with respect to the proportionate content of a component material in a combination or structure, "predominate" means the component constitutes the majority of the weight of the combination or structure.

Figure 5A:
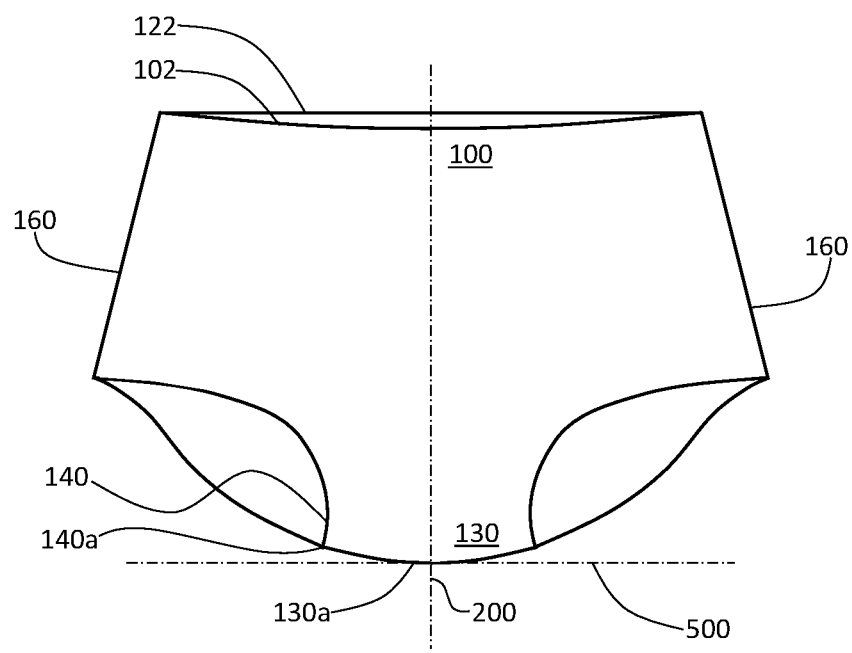
FIG. 5A is a simplified depiction of an example of a brief pant, as it would appear laid out flat on a horizontal planar surface, front waist portion facing up.
Figure 5B:
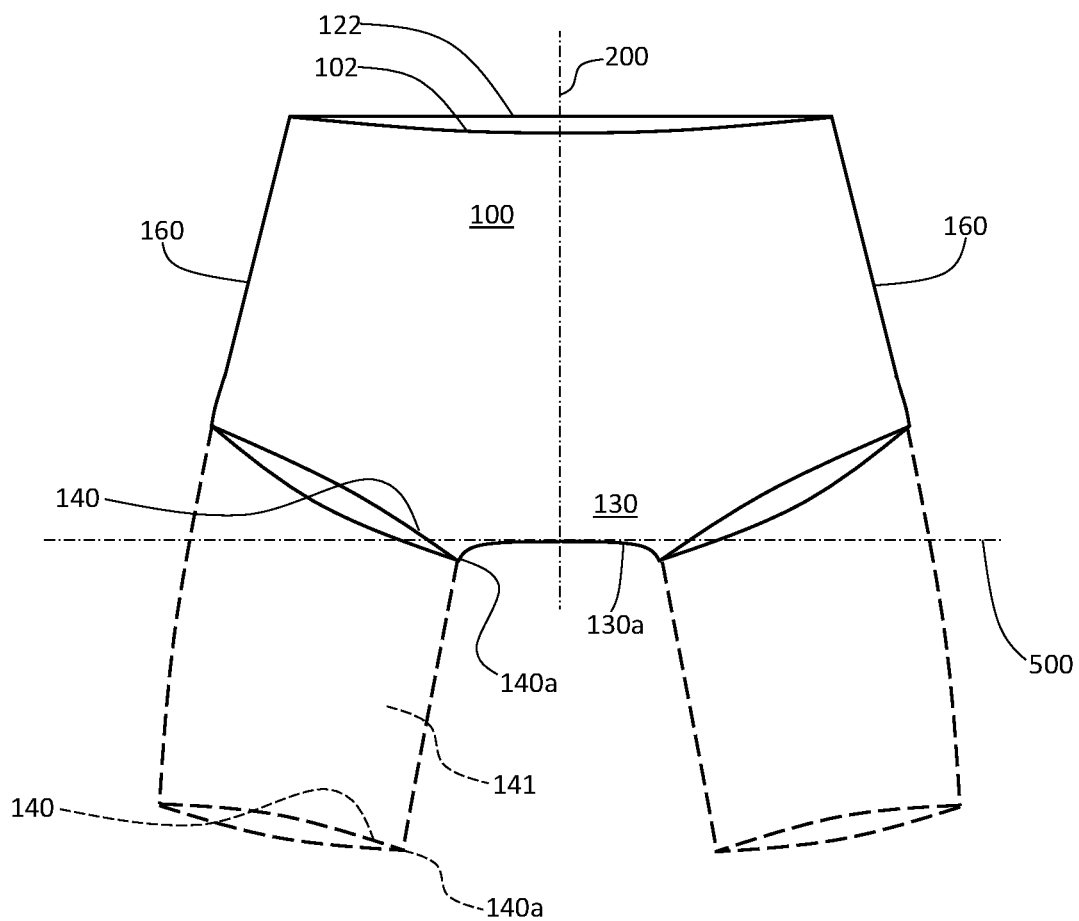
FIG. 5B is a simplified depiction of an example of a shorts pant (or legged pant), as it would appear laid out flat on a horizontal planar surface, front waist portion facing up.

For purposes herein, a "brief pant" is distinguished from a "legged pant" by the configuration of the inside leg edges, resulting from the manner in which the component materials are shaped, sized, proportioned and seamed or otherwise affixed together. FIG. 5A depicts an example of a brief pant and FIG. 5B depicts an example of a legged pant in alternative forms. When the garment in its assembled condition is laid out flat on a horizontal planar surface, front waist portion facing up, and a lateral crotch tangent line 500 is drawn perpendicularly to longitudinal axis 200 and tangent to the point at which the crotch portion lower profile 130a intersects the longitudinal axis 200, for a brief pant, the lowermost points 140a along the inside leg opening edges 140 are disposed along or above the crotch tangent line 500 (i.e., toward the front waist edge 102) (see FIG. 5A); and For a legged pant, the lowermost points 140a along the inside leg opening edges 140 are disposed below the crotch tangent line 500 (i.e., away from the front waist edge 102) (see FIG. 5B).

As reflected in FIG. 5B, for purposes herein, a legged pant may have leg portions 141 of any length, wherein the lowermost points 140a of inside leg opening edges 140 are disposed below the crotch tangent line 500. Underwear shorts pants such as "boy short" styles will generally have shorter leg portions as suggested in the solid-line portions of FIG. 5B, while other legged pants may have leg portions of varying lengths, as suggested by the dashed-line portions of FIG. 5B.

DESCRIPTION OF EMBODIMENTS

As noted in the Background, a problem presented in designing an absorbent system to be used to contain and absorb unintended (incontinent) small discharges of urine by a woman results from adhering urine flow. As a result of relatively low velocity of unintended discharges, female anatomical features, and typical surface chemistry of human skin (which can cause skin surfaces to attract and be relatively wettable by aqueous solutions such as urine), adhering flow has always been a phenomenon associated with low to moderate adult female incontinence. If features of a chosen containment/absorbency system do not reliably hold absorbent materials against the wearer's skin to intercept adhering flow, leakage can result.

It is believed, however, that a durable adult absorbent brief pant (i.e., a pant with a crotch portion including an absorbent structure and a liquid impermeable barrier layer to the outside thereof), that reliably protects against leakage of adhering flow through a variety of body movements and positions and over a reasonable duration of wear/use has not been marketed to date. Currently marketed pant products do not effectively hold included absorbent structures against the body through various body movements, over a reasonable duration of wear/use. It is believed that the garment industry to date has failed to recognize that suitably oriented elastic stretch is important for maintaining proximity and/or contact of the absorbent structure with the wearer's body contours and skin surfaces through various body positions and movements, and that a structure having a combination of absorbent capacity suitable for providing protection against leakage from light to moderate incontinence, while having suitable directional elastic stretch so as to maintain effective contact of the structure with the wearer's body, may be designed. The human body and particularly the female lower torso and crotch region have geometrically non-ruled contoured surfaces. Fabrics or web materials that do not exhibit an effective amount of elastic stretch capability along an effective direction will not effectively conform closely to (i.e., remain in contact with) the substantial majorities or entireties of these surfaces through ordinary body positions and movements. Increasing the amount of elastic stretch capability imparted to crotch gusset increases the variety of body shapes and movements to which the gusset can conform in use. In connection therewith, reducing the longitudinal tensile modulus (longitudinal tensile force in the material resulting from longitudinal stretching) tends also to increase body conformity and enhance comfort.

For underwear, many women prefer brief pants rather than legged pants such as "boy shorts" styles for ordinary daily wear. This is due to issues of comfort; unlike a legged, shorts-type pant, a brief pant ordinarily will not ride up and bunch about the legs from changes of body position, and thereby be a source of unwanted concentration of material bulk, tightness about the legs or other discomfort under outer clothing. Further, due to the manner in which their leg edges tend to cause the pant to fit through the crotch region of the body, brief pants having suitable elastic stretch characteristics may be preferred for maintaining a close fit about the female genital/urethra area, for purposes of protecting against leakage of unintended discharges of urine.

It has been learned that a durable absorbent pant may be designed that more reliably and comfortably holds an absorbent structure against/in contact with a wearer's body through the crotch region, in a position to better intercept adhering urine flow, capture the urine in the absorbent material before it can escape, and permit expansion of the absorbent components, initially and over a reasonable duration of wear/use of the pad. In order for a fabric or web of material to conform to a non-ruled surface, it must be capable of stretching along at least one direction. It has been determined that the direction of stretch that most effectively enables a fabric or web of a pant garment to effectively conform to the contours of the female lower torso and crotch region is, substantially, the longitudinal direction.

Figure 2A:
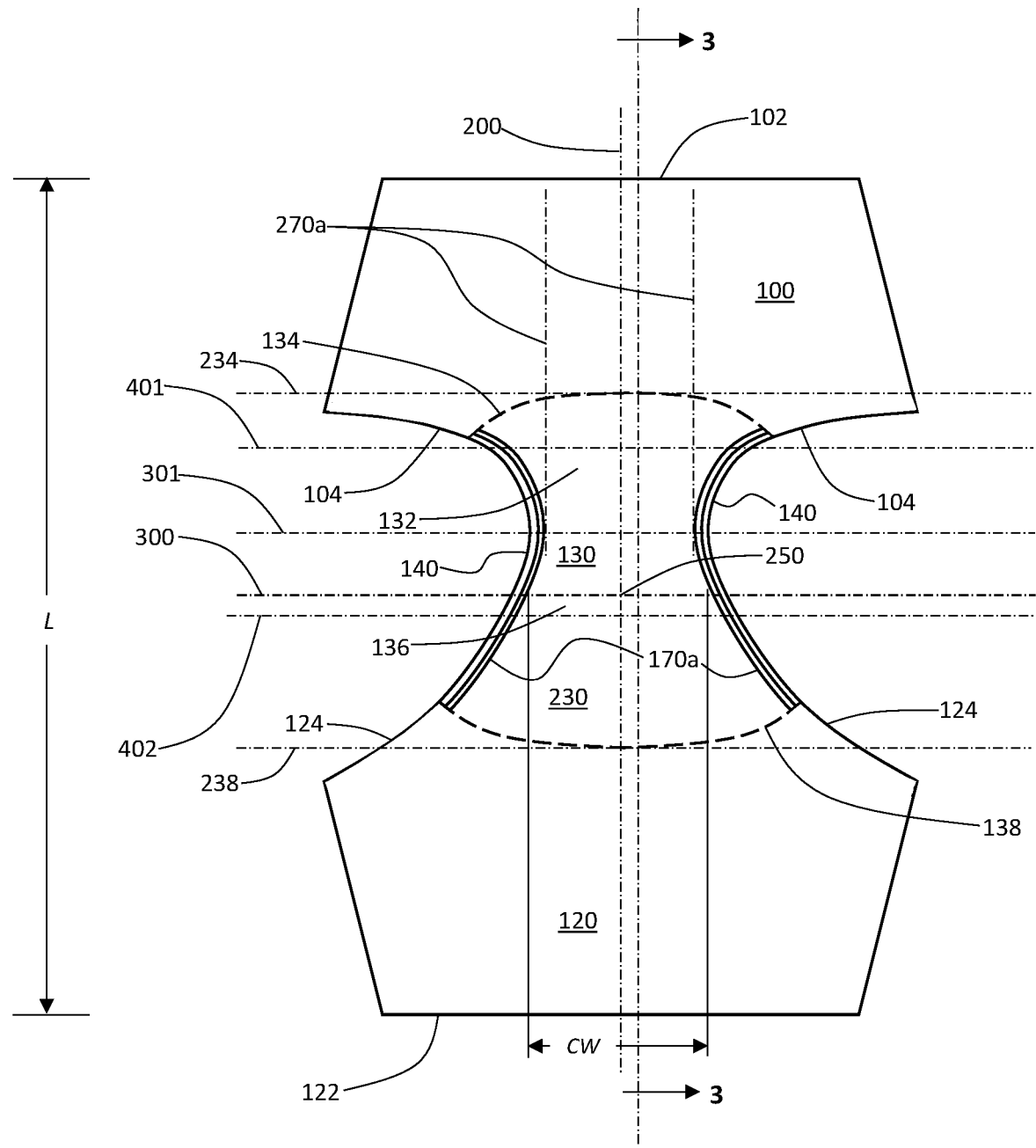
FIG. 2A is a depiction of one example of the brief pant of FIG. 1, in an opened configuration wherein the front and rear waist portions have been separated at the hip portions or hip side seams, as it would appear laid out flat on a horizontal planar surface, wearer-facing surfaces facing up.
Figure 2B:
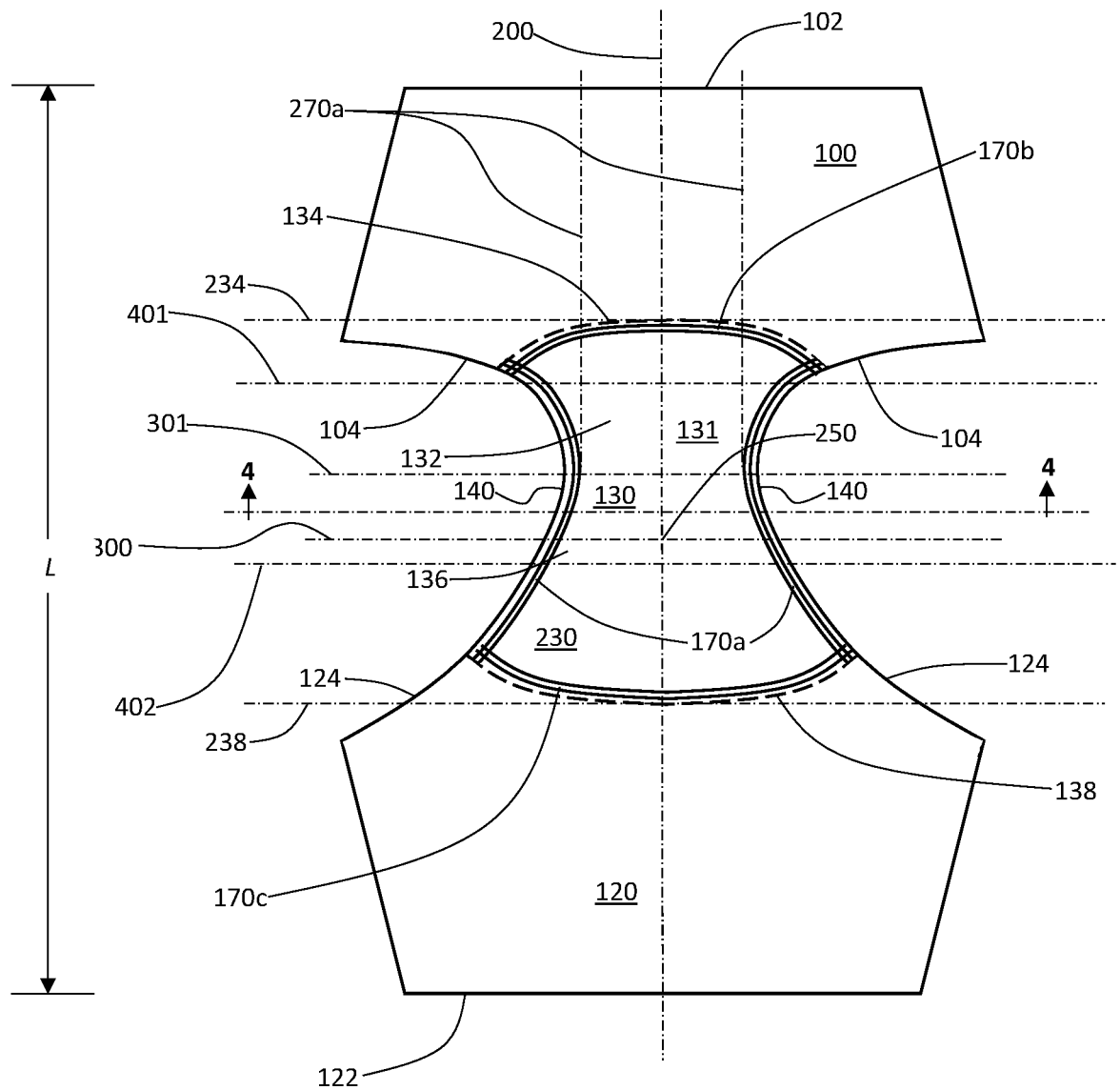
FIG. 2B is a depiction of another example the brief pant of FIG. 1, in an opened configuration wherein the front and rear waist portions have been separated at the hip portions or hip side seams, as it would appear laid out flat on a horizontal planar surface, wearer-facing surfaces facing up.

Referring to FIGS. 1, 2A and 2B as illustrative but non-limiting examples, a pant may include a front waist portion 100, a rear waist portion 120 and a crotch portion 130 bridging the front and rear waist portions. Front waist portion 100 has a front waist edge 102, and left and right front leg opening edges 104. Rear waist portion 120 has a rear waist edge 122, and left and right rear leg opening edges 124. Crotch portion 130 has left and right crotch leg opening edges 140. Crotch portion 130 may include or consist of a crotch gusset 230 that may include several layer components that will be described further below. (For purposes herein, the "crotch portion 130" is a portion of a pant identified as described herein, independently of specific components or structures. A "crotch gusset 230" is structural component that includes at least two distinct layers including an absorbent layer and a liquid impermeable barrier layer, and bridges the front waist portion 100 and the rear waist portion 120. A crotch gusset has a "liquid impermeable barrier layer" if it exhibits z-Direction Leakage no greater than 0.1 ml of test fluid into a section of filter paper, in the Liquid Impermeability test described below. Referring to FIGS. 2A and 2B by way of example, for purposes herein, crotch portion 130 is the portion of the pant, at a minimum, lying between crotch portion minimum front extent 401 and crotch portion minimum rear extent 402, longitudinally centered about crotch portion lateral axis 301 (which is drawn along the smallest width dimension CW measured between the crotch leg opening edges 140), plus 10 percent of the overall length L of the pant to the front and the rear of the crotch portion lateral axis 301. As suggested by FIGS. 2A and 2B, it may be desired that the crotch portion lateral axis 301 be disposed forward of the lateral axis 300 (which equally divides overall length L), rather than be co-located with lateral axis 300, for purposes of better fit about an adult female wearer's legs and lower torso. Thus, the respective boundaries between crotch portion 130 and front and rear waist portions 100, 120 for purposes herein are independent of the location(s) of any seams such as seams 134, 138 that may be present to join material(s) included in the crotch gusset 230 and material(s) included in the front and rear waist portions 100, 120.

Figure 3A:
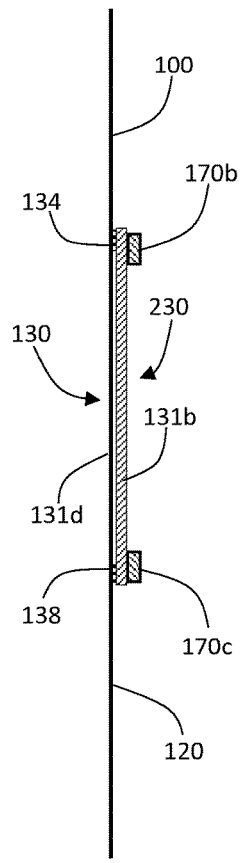
FIGS. 3A-3D are schematic longitudinal cross sections of various alternative examples of a brief pant as depicted in FIG. 2A, taken along line 3-3 in FIG. 2A.
Figure 3B:
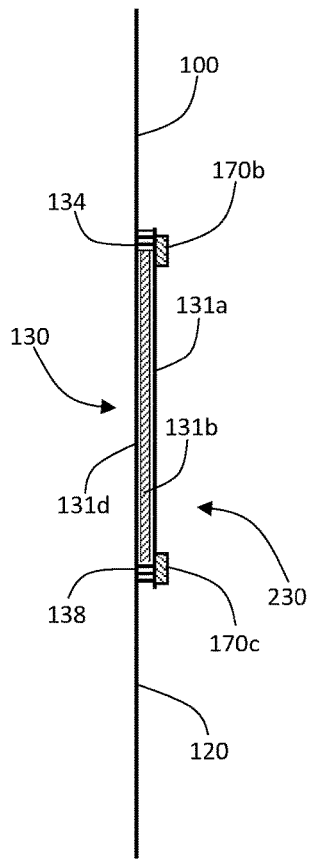

Material(s) forming one or both of forward and rearward portions 132, 136 of crotch portion 130 may be continuous with material(s) forming front and rear waist portions 100, 120, or alternatively, one or both of forward and rearward portions 132, 136 of crotch portion 130 and/or crotch gusset 230 may be substantially formed of one or more sections or layers of material that are distinct from material(s) substantially forming one or both of front and rear waist portions 100, 120, and crotch gusset 230 may be joined to front and rear waist portions 100, 120 at one or both of forward seam 134 and rearward seam 138. In illustrative but non-limiting examples reflected in FIGS. 3A and 3B, front waist portion 100, an outward-facing layer of crotch portion 130, and rear waist portion 120, may be formed partially or entirely of a first single, continuous section of material. In the example shown, one or more additional layers of material 131a, 131b may be added to crotch portion 130 on the wearer-facing side as shown, and be affixed to the first section of material via, e.g., stitching/sewing, adhesive bonding, thermal bonding (fusing or welding) or other suitable attachment/joining mechanism (hereinafter, attachment mechanism) at forward and rearward seams 134, 138.

Figure 3C:
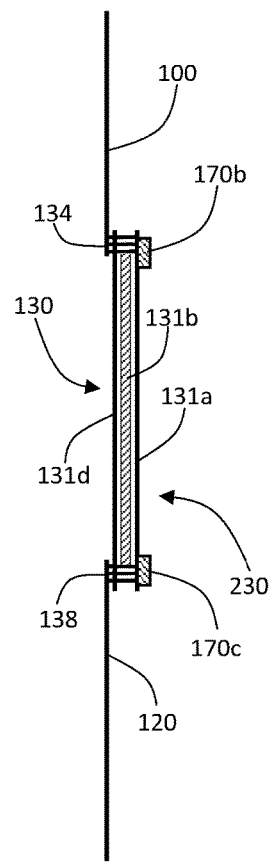
Figure 3D:
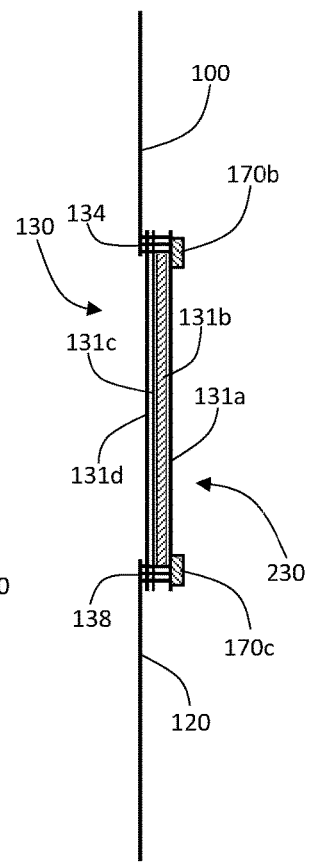
Figure 4:
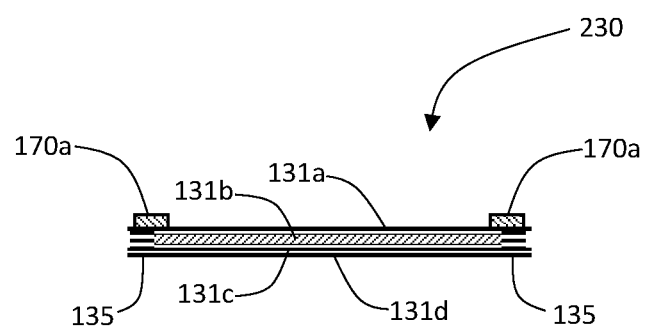
FIG. 4 is a schematic lateral cross section of an example of a brief pant as depicted in either of FIG. 2A or 2B, taken along line 4-4 in FIG. 2B.

In other illustrative but non-limiting examples, referring to FIGS. 3C and 3D, the sections of materials respectively forming front waist portion 100, rear waist portion 120 and crotch gusset 230 may be separate and distinct, and joined via any suitable attachment mechanism at forward and rearward seams 134, 138. A configuration approach schematically depicted by way of non-limiting examples in FIGS. 3C and 3D may be preferred because these approaches may provide the designer with greater flexibility in selection of the respective materials for the waist and crotch portions with respect to appearance, feel, weight, breathability, elongation, stretch characteristics and cost. The elongation and stretch characteristics described below would be applicable to the one, or more layers of material in combination, present in crotch portion 130 and/or crotch gusset 230.

Crotch Portion/Crotch Gusset

Width

It has been learned through experimentation that typical durable absorbent brief pants, currently marketed to wearers experiencing incontinence, do not have a crotch portion width that is sufficient for providing effective coverage and contact against the body through a variety of normal body positions and movements. Accordingly, it may be desired that the crotch portion 130 have a minimum width CW (see FIGS. 1 and 2A) of at least 7.0 cm, more preferably at least 7.5 cm, and even more preferably at least 8.0 cm.

Caliper

For purposes of minimized bulk, it may be desired that the combination of layered materials present in the crotch portion 130 and/or crotch gusset 230 be selected and configured so has to have a central z-direction Caliper not exceeding about 5 mm, more preferably not exceeding about 4 mm, and even more preferably not exceeding about 3.5 mm. (Herein, the "central z-direction Caliper" or "central Caliper" is measured at a location in the crotch portion 130 corresponding with the intersection 250 of the longitudinal 200 and lateral 300 axes of the pant, when opened and laid out flat on a horizontal planar surface.) Based on disclosure herein and teachings available in the art concerning textiles, persons of ordinary skill in the art will be equipped to select a combination of suitable materials to create a structure in the crotch portion 130 such as a crotch gusset 230 having such Caliper, along with other features and attributes described herein.

Absorption Capacity

In order for a durable absorbent pant to provide suitable absorbency and protection against leakage of unintended discharges of urine over a reasonable duration of wear, for a woman experiencing light to moderate incontinence, while balancing concerns for limiting caliper/bulkiness of the crotch portion while limiting the required relative planar size/surface area of an absorbent portion, it may be desired that a combination of material forming the structure within the crotch portion 130 of the pant have an Area Absorption Capacity from 0.1 ml/cm$^2$ to 0.4 ml/cm$^2$, and a Volume Absorption Capacity from 0.4 ml/cm$^3$ to 0.8 ml/cm$^3$, measured according to the Absorption Capacity Measurement method set forth below. Based on disclosure herein and teachings available in the art concerning textiles, persons of ordinary skill in the art will be equipped to select a combination of suitable materials to create a structure in the crotch portion 130 having such absorption capacity. It is believed, further, based on recent availability of fabric materials including yarns that include superabsorbent polymers (e.g., fabrics including "SAF" superabsorbent fiber, as available from Technical Absorbents Limited, Grimsby, United Kingdom), that a crotch portion may be configured to have a Volume Absorption Capacity greater than 0.8 ml/cm$^3$, e.g., up to 0.9 ml/cm$^3$, 1.0 ml/cm$^3$, 1.1 ml/cm$^3$, or even up to 1.2 ml/cm$^3$. Without intending to be found by theory, it is believed that materials such as these can provide Volume Absorption Capacity at such levels by swelling beyond their dry volumes, with absorbed liquid.

Elastic Stretch Attributes

Through experimentation it has been learned that imparting a pant with appropriate directional elastic stretch characteristics within the crotch portion 130 are important to provide a pant with a crotch portion that is both comfortably and securely held against the wearer's body surfaces, in position to intercept and absorb an adhering flow of urine, and thereby prevent leakage from the pant, through normal ranges of body positions and movements. It has been learned that the combination of materials present in the crotch portion 130 preferably should exhibit a maximum Longitudinal Elongation of 25 percent to 100 percent, measured according to the Maximum Elongation Measurement Method set forth below. Alternatively, or additionally, it may be desired that the combination of materials present in the crotch portion 130 exhibit a Longitudinal Tensile Modulus, measured according to the Longitudinal Tensile Modulus Method set forth below (reflecting the presence of one or more materials that impart elasticity) of 10 gf/mm to 100 gf/mm. Based on disclosure herein and teachings available in the art concerning textiles, persons of ordinary skill in the art will be equipped to select a combination of suitable materials to create a structure in the crotch portion 130 having such longitudinal elongation and tensile modulus properties.

Materials Selection

Generally, the front and rear waist portions 100, 120 of suitable examples of a pant may be formed of any fabric material or combination of fabric and other materials known and used as components of underwear, swimwear or athletic/active wear, exhibiting suitable attributes that may include, depending upon the location of the fabric within the structure, pleasing feel against the skin (softness and/or low-friction/smooth/silky feel), low caliper/bulk, elongation capability, elasticity, absorbency, wicking ability, breathability, etc.

Crotch portion 130 and/or crotch gusset 230, as herein described requiring absorbency and longitudinal elastic stretch attributes, may include a combination of several materials selected to impart the structure with the desired attributes.

Fabric Structure

Most durable fabrics exhibit anisotropic elongation capabilities.

Woven fabrics, formed by weaving, are formed of two groups (warp group and weft group) of interlaced constituent yarns or threads, the yarns or threads within each group being substantially parallel to each other, and substantially perpendicular to the yarns or threads in the other group, along the plane of the fabric. Unless the constituent yarns or threads are themselves formed of elastic material, woven materials have relatively low elongation capabilities along the warp and weft directions, and have relatively higher elongation capabilities along the two bias directions approximately 45 degrees from the warp and weft directions. Consequently, where it is desired for particular reasons that a layer component of the crotch portion 130 and/or crotch gusset 230 be a woven material, it may be desired that the material be oriented within the crotch portion such that one of the warp and weft directions is oriented from approximately 30 degrees to approximately 60 degrees, preferably from approximately 38 degrees to approximately 52 degrees, and more preferably approximately 45 degrees from the longitudinal direction of the pant, so as to provide maximum available longitudinal elongation capability for the woven layer.

However, when stretched along the bias direction, woven fabrics typically exhibit a substantial Poisson effect contraction along the trans-stretch direction (90 degrees from the stretch direction). When such a fabric is included in the crotch portion 130 with its bias oriented approximately along the longitudinal direction of the pant, the Poisson contraction effect may cause the crotch portion to laterally narrow, which may be deemed undesirable when full coverage of the wearer's crotch region is desired.

The constituent yarns or threads of knitted fabrics, by contrast, do not follow straight paths along the plane of the fabric, and are neither parallel nor perpendicular to each other. Rather, each constituent yarn or thread of a knitted fabric follows a looping path along successive rows, interlooping with one or more constituent yarns or threads in adjacent rows. As a consequence, knitted fabrics exhibit relatively greater elongation capability along all directions as compared with woven fabrics, even where the constituent yarns or threads themselves are not elastic. For this reason, unless a woven fabric is desired for a particular reason, it may be preferred that a knitted fabric be used to form any one or more, or all, of the fabric layers present in the crotch portion 130 and/or crotch gusset 230 of the pant.

Even so, most types of knitted fabrics have elongation capabilities that are anisotropic along the plane of the fabric, having a first direction of greatest elongation capability and a second direction, perpendicular to the first direction, of least elongation capability. Accordingly, when knitted fabric is selected and used to form one or more layers present in the crotch portion 130 and/or crotch gusset 230 of the pant, it may be desired that the fabric(s) forming any, some or all of the layers be oriented such that their directions of greatest elongation capability are at least approximately parallel with the longitudinal direction of the pant.

In some circumstances it may be desired that a knitted fabric selected to form a layer be a rib knit type. Rib knitted fabrics exhibit relatively high elongation capability along a direction parallel to the knit rows (perpendicular to the "ribs"), with relatively low Poisson contraction effect along the trans-stretch direction. Thus, in some circumstances, it may be desired that one or more layers present in the crotch portion 130 and/or crotch gusset 230 of the pant be formed of a rib knit fabric, with the "ribs" oriented substantially along the lateral direction of the pant.

In some circumstances it may be desired that the absorbent layer be formed of either woven or knitted terrycloth, for purposes of increasing aggregate fiber surface area and capillarity per unit fabric surface area, and thereby, providing increased absorbency to the absorbent layer 131b, while still providing a durable fabric, in contrast to a nonwoven batt or matt of fibers. In conjunction therewith or as an alternative, and for purposes of enhancing absorbency, it may be desired that constituent fibers of the yarn(s) or thread(s) from which the absorbent layer fabric material is knitted or woven be in the form of microfibers (i.e., fibers having an average denier of one (1) or less). It may be further desired that the constituent fibers be split microfibers. Yarns or threads formed of microfibers, particularly split microfibers, provide relatively greater fiber surface area per unit yarn/thread denier. When the fiber surfaces are hydrophilic, this imparts relatively greater absorbency to the fabric.

Fabrics Constituent Yarn/Thread Compositions

As contemplated herein, wearer-facing 131a and absorbent 131b layers present in the crotch portion and/or crotch gusset of the pant are expected to be exposed to discharges of urine, and are expected to receive, absorb and retain the urine for a reasonable duration of wear time, preferably while leaving the wearer-facing surfaces as dry-feeling as possible. It may be desired that a wearer-facing layer 131a have a soft feel against the skin.

Accordingly, it may be desired that the wearer-facing layer be formed of a material that has a soft feel and has suitable wicking attributes so as to efficiently conduct discharged urine to an absorbent layer beneath, while having minimized tendency to retain urine and thereby have a wet feel for the wearer. Suitable materials may include polyesters and polyamides (e.g., nylon). Examples of these materials, when used to spin fiber components and/or when having received suitable hydrophilizing treatment, impart the spun fibers with suitable hydrophilic surface attributes (enhancing wicking), with relatively low individual fiber texture (reducing porosity and capillarity, and therefore, absorbency of the fabric). Additional materials may be incorporated in yarn or thread components for purposes of enhancing skin feel (e.g., enhancing a slick or silky feel against the skin) and/or further affecting hydrophilicity and/or reducing absorption tendencies. In some examples, polypropylene and/or polyethylene fiber components may be included for these purposes. In some examples, resins from which constituent fibers are spun may include additives to the primary polymer components, incorporated for enhancing skin feel, adjusting hydrophilicity, reducing absorbency, etc. In some examples, polyester or nylon component resins may include an additive comprising linolenic acid, to the extent of and as described in US 2017/0369698, for purposes of enhancing elongation and skin feel attributes, while reducing material usage and cost.

Although commercially processed cotton or other commercially processed natural fiber, or semi-synthetic, cellulose-derived materials such as rayon, may be used or included as the component material for the absorbent layer for their inherent absorbency attributes, these materials may have a tendency, undesirably, to retain constituents of urine and/or other discharged fluids following laundering. Accordingly, one or more of polyester, polyamide and/or combinations thereof may be preferred as component resins or even the main/predominate component resins from which fiber components of yarn or thread components of fabrics for the absorbent layer 131a are formed.

For purposes of imparting elasticity to layers present in the crotch region (particularly longitudinal stretch elasticity), it may be desired that yarn or thread components of one or more of the fabrics present include elastic fibers, yarns or threads. In some examples, elastic fibers, yarns or threads may be formed of or include elastane or spandex (such as LYCRA, currently available from The LYCRA Company, Wilmington, Delaware), which are particularly elastic and durable through a plurality of launderings, as compared to other elastic materials used to elasticize fabrics.

In other examples, one or more elastic polymer film layers distinct from the fabric layer(s) in the crotch portion 130 may be included to impart elasticity to the structure in the crotch portion as a whole.

An elastic polymer film layer may be formed of any suitable elastic polymer material. In some examples, an elastic film layer may be formed by extrusion or other application of film resin in molten or semi-molten form onto a layer component fabric, whereby the molten resin partially penetrates the fabric and upon cooling forms a film that is partially mechanically enmeshed in and/or made integral with the fabric.

Antimicrobial Agents

For purposes of hindering growth of microorganisms supported by absorbed urine, which may cause odor, it may be desired to include one or more antimicrobial agents in or among the materials present in the crotch portion 130. Any such antimicrobial agents are preferably included in a form adapted to remain in place and continue to be effective following a plurality of launderings of the pant. In some examples, an antimicrobial agent may include particles of a metal, metal alloy or metallic compound that includes one or more of copper, silver, zinc, aluminum or combinations thereof. In other examples an antimicrobial agent may include particles of carbon or a composition or compound including carbon. One or more of these materials may be included as additives to resins from which constituent fibers are spun, or may be included in compositions that are topically applied to constituent yarns, threads or fabrics following manufacture thereof. Such antimicrobial agents are preferably included in material(s) forming the absorbent layer 131b and/or the wearer-facing layer 131a.

Barrier Layer

When urine is absorbed in a fabric layer in the crotch portion 130 and/or crotch gusset 230, it may be desirable to include a barrier layer, e.g., barrier layer 131c (FIG. 3D) to prevent the absorbed urine from passing from the absorbent layer to an outer fabric layer 131d or even to outer clothing. In some examples, a barrier layer may be formed of or include a suitable liquid impermeable polymer film. In some examples, the film composition may be selected to have elastic elongation capability, providing suitable elastic stretch attributes to the combination of layers present in the crotch portion 130 and/or crotch gusset 230. In one example, a barrier layer 131c may comprise a film formed in whole or in part of a polyurethane- or polyester-based resin. In another example, a barrier layer 131c may comprise a film that is formed by extrusion or other application of thermoplastic film resin in molten or semi-molten form directly onto the outward-facing surface of an overlying layer, such as absorbent layer 131b, such that the film resin while still molten partially penetrates the fabric and thereby forms a liquid impermeable film that is partially mechanically enmeshed in and/or made integral with the fabric. This also has the effects of consolidating layers, which can reduce caliper in the crotch portion 130, and reducing or preventing wrinkling or bunching of the absorbent layer 131b upon elastic contraction. In a particular example, a polyurethane or polyester film may be formed by extrusion or other application of molten thermoplastic resin directly onto an outward-facing surface of a fabric that serves as or forms a component of absorbent layer 131b.

The material selected for the barrier layer may also be vapor permeable or "breathable" in that it can permit gas or water vapor to pass therethrough, while still being effectively liquid impermeable under ordinary conditions of the use contemplated herein, via a combination of having a porous structure for vapor permeability, but sufficiently small pore sizes and surfaces having low wettability (e.g. hydrophobic surfaces), for liquid impermeability. Various liquid impermeable, vapor permeable films and other materials are known and used in fields including personal hygiene, garment and wound dressing applications. A liquid impermeable but vapor permeable barrier layer may be preferred in some circumstances for purposes of venting water vapor to improve wearer comfort and/or help avoid overhydration of the wearer's skin. A monolithic thermoplastic elastomeric (TPE) film material may be desired for the barrier layer, for having stretch/elasticity characteristics and breathability.

It may also be desired in some examples that the material selected for the barrier layer be able to withstand application of heat, where used to bond the barrier layer to an overlying fabric layer, such that the material will not develop holes therethrough during the bonding process (which can compromise liquid impermeability). In some examples, a suitable barrier layer material for the above-mentioned purposes may include polyethylene terephthalate (PET), or thermoplastic polyester elastomer (TPEE). The material may be obtained in the form of a monolithic film and may be applied and bonded to a fabric layer via application of heat.

Other Construction Details

Figure 7A:
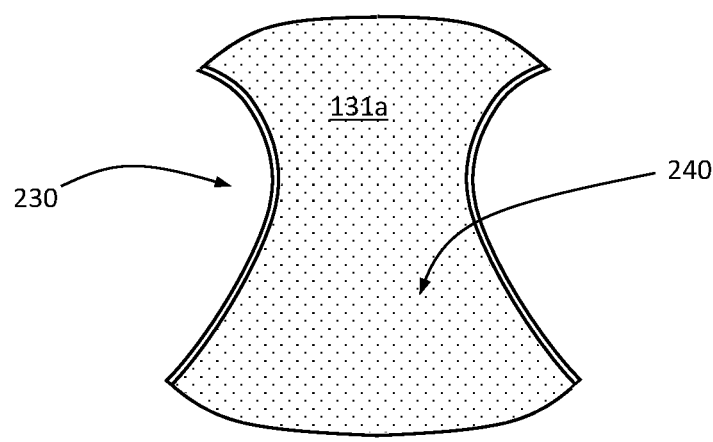
FIG. 7A is a plan view of an example of a crotch gusset laid out on a horizontal surface, wearer-facing surface facing the viewer.
Figure 7B:
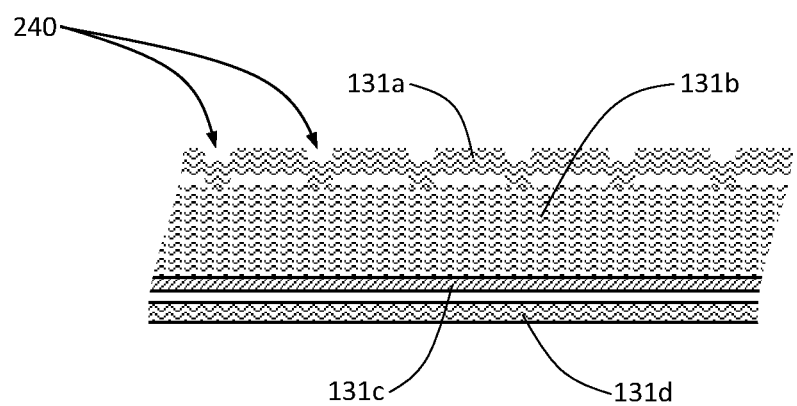
FIG. 7B is a schematic vertical cross section of a portion of the gusset shown in FIG. 7A.

In some examples one or more layers within the crotch portion 130 and/or crotch gusset 230 may be bonded together via any suitable bonding mechanism. Referring to FIGS. 7A and 7B for example, a wearer-facing layer 131a may be bonded to a subjacent absorbent layer 131b for purposes of holding the layers in close proximity and thereby helping maintain a desired low caliper of the structure, and enhancing fluid communication between the layers, i.e., enhancing the structure's ability to pass discharged urine from the wearer-facing layer to the underlying absorbent layer, via contact between the layers. In such example, the bonding mechanism should be selected so as not to occlude the interface between the two layers along any substantial portion of their interfacing surface areas. Thus, in some examples it may be desired that the bonding mechanism have the form of a discontinuous pattern of discrete bonds (i.e., a pattern with unbonded regions between the bonds), such as a regular pattern of spot bonds 240. In some examples, bonds between the layers may be formed by discrete deposits of adhesive between the layers, adhering them together at the locations of the deposits. In other examples, bonds between the layers may be formed by thermal compression bonding. The latter bonding mechanism may be more durable through a plurality of launderings, and as illustrated schematically in FIG. 7B, creates a corresponding pattern of z-direction depressions in the wearer-facing layer 131a that may serve to collect discharged urine/fluid and initiate and/or facilitate its movement (via wicking) down to the absorbent layer 131b. For purposes of enabling thermal compression bonding, the wearer-facing layer and the subjacent absorbent layer may each include polymer components of respective fusible compositions (such as similar polyester-based compositions) that facilitate formation of robust bonds between the layers upon localized application of heat and pressure at the bond sites. (Herein, "fusible compositions," with respect to two respective polymers present in two respective layers, means that the two polymers are miscible, capable of melting and mixing at a temperature of 250° C. or lower, to form a single thermodynamic phase.)

Various layers that may be included in crotch portion 130 and/or crotch gusset 230, e.g., layers 131a, 131b, 131c and 131d, may also be joined to each other by any suitable mechanism at forward and rearward seams 134, 138 and crotch side seams 135 proximate the leg edges 140. The joining mechanism may be a system of stitching to affix the layers together; however, for purposes of liquid containment it may be desired that the joining mechanism include a generally hydrophobic, water insoluble adhesive, by itself or as a supplement to stitching.

Containment Barriers

Referring to FIGS. 2A, 2B, 3A-3D and 4, for purposes of reducing chances that adhering urine flow may escape to locations beyond overlying absorbent portions of the crotch portion 130 of the pant during wear, it may be desired to include one or more sections of containment barrier 170a, 170b, 170c. A containment barrier may be formed of any material suitable for creating a defined hydrophobic zone that resists wetting and flow of urine thereover, or even a barrier or wall structure extending from the wearer-facing surfaces of the pant toward the wearer's skin and defined by a greater z-direction Caliper relative the central z-direction Caliper of the crotch portion 130 (i.e., at the intersection 250 of the longitudinal 200 and lateral 300 axes of the pant).

As suggested in the figures, a pair of side containment barriers 170a may be located along the inside leg edges 140 of a brief panty (see, e.g., FIGS. 2A and 4), and may be configured to follow the curvature of the leg edges 140. In other examples (not shown), side containment barriers may have other configurations, including but not limited to following straight lines or paths, or curvatures other than that of the leg openings.

Front 170b and/or rear 170c containment barriers may be located, respectively, proximate front and/or rear extents 401, 402 of the crotch portion 130 (see, e.g., FIGS. 2B and 3A-3D.) In some examples as suggested in FIG. 2B, a system of containment barriers may substantially or entirely circumscribe the intersection 250 of the longitudinal 200 and lateral 300 axes of the pant, and may substantially or entirely circumscribe the crotch portion 130. In some examples, a continuous containment barrier having effectively joined portions 170a, 170b, 170c may entirely circumscribe the intersection 250 of the axes, and may follow a path defining a circular shape, oval shape, stadium shape, rounded rectangle shape, peanut shape, hourglass shape or any other desired shape, substantially or entirely circumscribing the intersection 250. For purposes of minimizing chances of leakage, it may be desired that a continuous containment barrier entirely circumscribe the intersection 250.

A containment barrier may be formed substantially of a hydrophobic material, for purposes of resisting wetting and flow of urine thereover and/or therearound.

In some examples, a containment barrier may be formed of a bead of hydrophobic polymeric material applied in fluid form to the wearer-facing surface of the pant, and then solidified. In a more particular example, a containment barrier may be formed of a bead of a hydrophobic silicone-based compound applied in fluid form and allowed to cure, dry or otherwise solidify in place. In some examples flocking may be applied to the bead while it is tacky (before it cures/solidifies), to adhere to the bead and reduce a "rubbery" feel and/or impart a cloth-like, velvet-like or otherwise pleasant feel to the bead.

In other examples, a containment barrier may be formed of a strip of hydrophobic film, hydrophobic closed-cell polymeric foam, or hydrophobic fabric affixed to the wearer-facing surface of the pant, e.g., by a flexible, extensible, hydrophobic adhesive. A variety of suitable hot melt adhesives are commercially available. In still other examples, a containment barrier may be formed of a strip of hydrophobic film, hydrophobic closed-cell polymeric foam, or hydrophobic fabric affixed to the wearer-facing surface of the pant via thermal compression bonding. In any or all of these examples, the material used to form the containment barrier may be selected to have elongation or elastic elongation attributes so as not to substantially reduce elastic elongation capabilities of the assembled layers present in the crotch portion 130.

In another example, a strip of hydrophobic tape (not shown) may be affixed via adhesive along the inside leg opening edges 140, and wrapped about the edges and around the outward-facing layer 131*d*, thereby sealing the edges of the layers at the leg edges and providing wearer-facing strip along the leg openings that hinders urine flow thereover. The hydrophobic tape may be selected for having not only hydrophobic, but also elastic elongation properties. In a particular example, the hydrophobic tape may be a silicone-based polymer tape.

EXAMPLES

Quantities of prototype brief pants were manufactured to include a crotch gusset, having the following layers, in order of wearer-facing (upper) layer to outward-facing (lower) layer:

Wearer-facing layer: Knitted fabric, 66% polyester, 34% polypropylene; direction of greatest elongation oriented longitudinally;

Absorbent layer: Knitted sheared pile terrycloth/sheared pile fabric, 86% polyester microfiber yarn, 14% nylon microfiber yarn; nylon yarn treated with antimicrobial agent including copper particles; sheared pile side facing wearer; direction of greatest elongation oriented longitudinally; and Barrier layer: Polyurethane film, extruded onto outward-facing surface of absorbent layer; and Containment barrier: strip of hydrophobic silicone-based film applied to entirely circumscribe the crotch portion, along the inside leg edges and forward and rearward seams.

Outward-facing layer: knitted fabric, 76% nylon, 24% elastane.

For purposes of comparison, crotch gussets of examples of SPEAX (formerly ICON) brand absorbent brief pants (a product of Thinx Inc., New York, New York), currently marketed to women experiencing incontinence, were measured and tested, according the methods described herein, for Maximum Longitudinal Elongation, Longitudinal Tensile Modulus, Area Absorption Capacity and Volume Absorption Capacity. For further comparison, crotch gussets of currently marketed KNIX brand absorbent pants (product of Knix Wear Inc., Toronto, Ontario, Canada) and MODIBODI brand absorbent pants (a product of Modibodi, Balmain, A U and Nashville, TN, USA) (both currently marketed as menstrual pants), were measured and tested. The results of the measurements/testing are set forth in the table below. (The comparison products did not include any containment barrier structures, but the crotch gussets were removed from the rest of the underwear keeping the bonding around the crotch portion intact, with the outer layer fabric being removed for the absorption capacity testing.)

|  | SPEAX (marketed as incontinence pant) | KNIX (marketed as menstrual pant) | MODIBODI (marketed as menstrual pant) | Prototype |
|---|---|---|---|---|
| Crotch Width CW (cm) | 7.2 | 6.5 | 7.7 | 8.0 |
| Dry Central Caliper (mm) | 5.2 | 2.0 | 2.9 | 3.4 |
| Area Absorption Capacity (ml/cm$^2$) | 0.29 | 0.11 | 0.20 | 0.25 |
| Volume Absorption Capacity (ml/cm$^3$) | 0.57 | 0.50 | 0.69 | 0.73 |
| Maximum Longitudinal Elongation (percent) | 5.3 | 5.9 | 20.3 | 38.0 |
| Longitudinal Tensile Modulus (gf/mm) | 497.7 | 454.7 | 157.4 | 53.4 |

Figure 6:
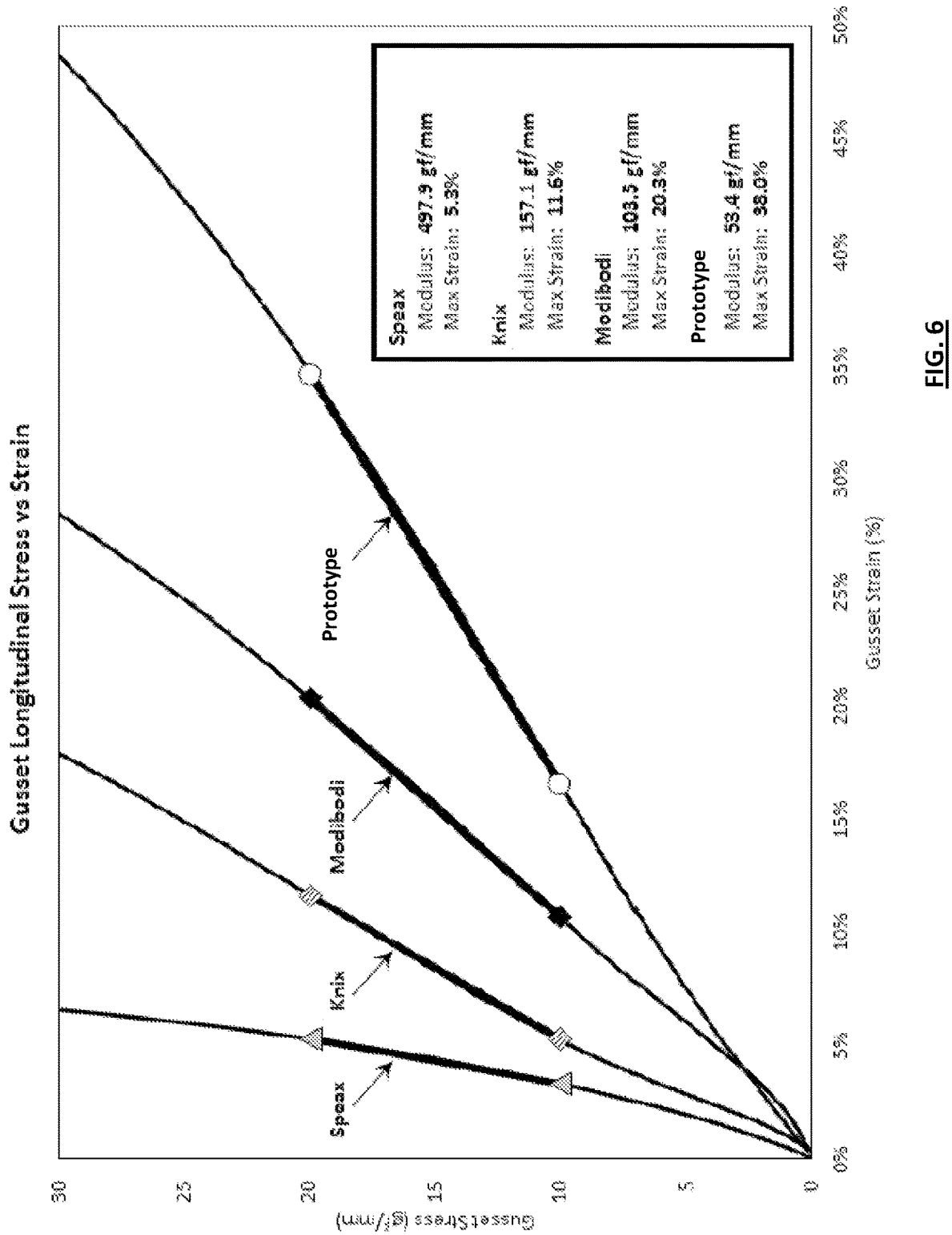
FIG. 6 depicts plots of stress (y-axis) vs. strain (x-axis) measured for crotch gussets of various examples of brief pants.

To graphically illustrate the differences between the elongation and tensile modulus characteristics of the prototypes as compared to examples of commercially available pants, the gusset longitudinal stress vs. strain are graphed in FIG. 6.

In consumer research, users indicated that the prototype pants provided greater comfort and superior leak protection as compared with the SPEAX product.

Measurement Methods

General Sample Preparation

Unless otherwise specified below, each of the measurements below is to be conducted on 10 separate like samples (taken from 10 separate like examples of pants) and the average of the 10 separate like samples is considered to be the measurement for that specific sample set.

Samples including the entire crotch gusset 230 are collected from examples of the subject pant. Lateral lines 234, 238 that are respectively tangent the forwardmost edge of the forward seam 134 and rearwardmost edge of the rearward seam 138 are identified, and the pant is cut apart along these lines (without cutting into the seam itself) to provide a sample that includes the entire crotch gusset 230 and perimeter containment barriers 170a, 170b and 170c (if included).

If the pant is a legged pant, cut out the gusset in its entirely, along cutting paths outside of the seam(s) joining the gusset to the remainder of the pant, without cutting into the seams themselves. For legged pants, measurements of "Crotch Width" made for purposes herein will be the width of the removed gusset measured along the lateral direction, along a lateral line marking the shortest distance between the leg openings prior to removal of the gusset from the legged pant.

The sample should be cut from the example pant with a sharp knife or suitably sharp cutting device effective to precisely and cleanly cut the sample. A straight edge or other suitable drafting/drawing tool may be used where helpful to hold the example down on the work surface and help guide the cutting device.

The testing is performed under ambient room conditions (temperatures from between 15° C. to 35° C. and relative humidity from between 35% to 75%). Samples are conditioned for at least two hours prior to testing under the same conditions.

All linear dimensions are measured manually by ruler within the ordinary x-y plane, using a ruler that is traceable to NIST or other standards organization.

Longitudinal Tensile Modulus

For the Longitudinal Tensile Modulus and Maximum Longitudinal Elongation test methods, the samples as described above in "General Sample Preparation" are further modified by cutting out a 40 mm laterally wide section symmetrically about the longitudinal axis 200. The perimeter containment barriers 170a are not included in these tests. If the lateral width between the narrowest separation of containment barriers 170a as defined by the tangent lines 270a in FIGS. 2A and 2B is less than 40 mm, then the pant is not deemed to be suitable for purposes described herein, and is considered to be outside the scope of the claims.

The Longitudinal Tensile Modulus of the sample is determined by stretching along the direction of the longitudinal axis 200 of the pant, using a constant rate of extension tensile testing machine with computer interface, e.g., Instron; MTS; Zwick; etc., using a load cell for which the loads measured are within 10% to 90% of the limit of the cell, and ensures accuracy of a 5N load to 0.1N. The instrument is equipped with a single line contact grips, 8 cm in grip width. Prior to testing, calibrate the equipment according to the instruments manufacturer's recommendations.

In accordance with the sample preparation instructions set forth above, the Sample Width is 40 mm. The stress in the sample is calculated by dividing the force in the load cell by the Sample Width, and is expressed in units of gf (grams-force)/mm. (The caliper of the sample is not a factor in this calculation.) The Sample Length is equal to the length of the sample along the longitudinal axis 200 between the lateral lines 234, 238 (along which the sample was cut from the example pant), as illustrated by way of example in FIGS. 2A and 2B.

The grips of the tensile testing machine consist of air actuated grips designed to hold the sample. No slippage should be permitted between the sample and the grips. The distance between the grips (along the axis of the machine's elongation) should be the Sample Length minus 6 cm. This distance will be hereinafter referred to as the "Starting Gauge-Length".

The sample is mounted in the grips with its longitudinal axis 200 parallel to the direction of applied elongation, and centered in each grip. Two (2) cm of the sample's length at each end is inserted into each grip. The Starting Gauge Length, determined as described above, will ensure that 2 cm of longitudinal slack will be present in the sample at the start of the test.

After the sample is mounted, the machine's load channel is set to zero (this eliminates the weight of the sample in the calculations). The grips are slowly moved apart at 5.08 cm/min (2.0 in/min) until a load of 5 gf (grams-force) is reached. The separation between the grips at this position is recorded as L0.

(L0=Starting Gauge Length+additional machine extension to reach 5 gf)

After the 5 gf load is reached, extend the sample at a rate of 50.8 cm/min (20 in/min) with a data acquisition rate of 50 Hz. Extend until either a stress of 30 gf/mm is reached, or the sample breaks.

Sample strain is calculated by $\Delta L/L0$. $\Delta L$ is any additional extension between the grips after L0 is reached and is recorded along with load at a rate of 50 Hz. Sample strain is expressed numerically (not as a percentage), thus a strain of 100% is 1.0 for the purposes of these calculations.

Record the sample strains at sample stresses of 10 gf/mm and at 20 gf/mm.

Longitudinal Tensile Modulus is the linear slope between 10 gf/mm and 20 gf/mm, and is calculated as:

Longitudinal Tensile Modulus=[20 gf/mm−10 gf/mm]/[sample strain at 20 gf/mm−sample strain at 10 gf/mm]

Repeat for 10 samples.

Maximum Longitudinal Elongation

Maximum Longitudinal Elongation is measured during the Longitudinal Tensile Modulus test. The Maximum Longitudinal Elongation is the sample strain at a sample stress of 20 gf/mm. Maximum Longitudinal Elongation is expressed as a percent strain, e.g., a value of 1.0 strain from the Longitudinal Tensile Modulus method is expressed as 100% strain for Elongation.

Repeat and record the results for 10 samples. Calculate and record the average of the results. The average will be the Maximum Longitudinal Elongation value for the subject pant design.

Absorption Capacity

The absorption capacity test measures the amount of liquid held within a test sample after specified times of immersion and vertical drainage. The amount of test liquid that is retained by the test sample is used to calculate and report the Area Absorption Capacity (milliliters (ml) of liquid per specimen area in square centimeters) and the Volume Absorption Capacity (in milliliters (ml) of liquid per specimen volume in cubic centimeters). All testing is performed in a room controlled at 23° C.±3C° and 50%±2% relative humidity.

The test procedure follows compendial method WSP 010.1.R3 (12) part B (Liquid Absorptive Capacity) with modifications specified as follows. The test liquid is deionized water at room temperature (23° C.±3C°; density 1.00 g/ml). For the weighing portions of the test, no cover glass is used as the test liquid is non-volatile. The overall dimensions of the wire gauze test specimen support is large enough (e.g. 12 inches by 12 inches) to accommodate the larger test sample size. The test sample is the entire gusset (as described herein), thus larger than what is suggested in the compendial method.

Prior to measuring absorption capacity, the examples of the pants of interest (prior to removal of samples therefrom) are washed in order to mimic in-use conditions and to follow the recommended "prior to use" instructions that accompany these types of pants (e.g. wash before use). The examples are placed into a mesh lingerie bag, and then placed into a high efficiency, front-loading washing machine (any convenient source) along with a single small/light load dosage of TIDE brand laundry detergent ("Original" designation; "HE" or other high efficiency washing machine designation; without additives such as FEBREZE, ODOR DEFENSE, OXI additives, bleach or bleaching additives or fabric softening additives) (product of The Procter & Gamble Company, Cincinnati, Ohio). The washer is set to delicate cycle using cold water. After the wash cycle, the examples are removed from the mesh bag and placed flat on a drying rack to air dry for about 12 hours. After air-drying, the examples are placed into a clothes dryer (any convenient source) set on the delicate cycle with very low heat for about 5 minutes or until dry to the touch.

Test samples are prepared as follows. The pre-washed and dried examples are equilibrated in a room controlled at 23° C.±3C° and 50%±2% relative humidity for about 2 hours. Test samples that include the entire gusset are removed from the examples as described in the General Sample Preparation section herein. Using scissors, the outermost fabric layer on the outward-facing side of the gusset is cut out along the entire gusset shape, inboard of the seams, using care so as not to cut into any of the edge seams present.

The immersion and drainage procedure outlined in the compendial method is then followed with the modifications previously noted. Subtract the Dry Mass from the Wet Mass and record as Liquid Mass Absorbed to the nearest 0.01 grams. Since the density of deionized water is 1.00 g/ml, the Liquid Mass Absorbed is also recorded as Liquid Volume Absorbed to the nearest 0.01 ml. Divide the Liquid Volume Absorbed (ml) by the overall area (cm$^2$) of the test specimen and record as Area Absorption Capacity to the nearest 0.01 ml/cm$^2$. Now divide the Liquid Volume Absorbed (ml) by the volume of the test specimen (area×central caliper) and record as Volume Absorption Capacity to the nearest 0.01 ml/cm$^3$. (Note: For purposes herein the area and central caliper of the test specimen is measured with the test specimen in a dry condition following sample preparation as described above, and in accordance with the Caliper measurement method set forth below.)

In like fashion, repeat for a total of three replicate test specimens. Calculate the arithmetic mean for Area Absorption Capacity and Volume Absorption Capacity and report to the nearest 0.01 ml/cm$^2$ and 0.01 ml/cm$^3$, respectively.

Caliper

The Caliper of a sample including a crotch gusset is measured as the distance between a reference platform on which the sample rests and a pressure foot that exerts a specified amount of pressure onto the sample over a specified amount of time. All measurements are performed in a laboratory maintained at 23° C.±2 C.° and 50%±2% relative humidity.

Caliper is measured with a manually-operated micrometer equipped with a pressure foot capable of exerting a steady pressure of 0.5 kPa±0.01 kPa onto the test sample. The manually-operated micrometer is a dead-weight type instrument with readings accurate to 0.001 mm. A suitable instrument is Mitutoyo Series 543 ID-C Digimatic, available from VWR International, or equivalent. The pressure foot is a flat ground circular movable face with a diameter of 50 mm. The sample is supported by a horizontal flat reference platform that is larger than and parallel to the surface of the pressure foot. The system is calibrated and operated per the manufacturer's instructions.

Obtain a sample including the gusset by removing it from the pant, as described above. When excising the sample from an absorbent article, use care to not impart any wrinkles into the layers or other distortion of the layers during the removal process. Samples are conditioned at 23° C.±2 C.° and 50%±2% relative humidity for 2 hours prior to testing. To measure caliper, first zero the micrometer against the horizontal flat reference platform. Place the sample on the platform with the desired measurement location centered below the pressure foot. Gently lower the pressure foot with a descent rate of 1.0 mm±0.1 mm per second until the full pressure is exerted on the sample. Wait 5 seconds and then record the caliper of the sample to the nearest 0.01 mm. In like fashion, repeat for a total of 10 replicate samples. Calculate the arithmetic mean for the Caliper and report to the nearest 0.01 mm.

Liquid Impermeability

When there is a question concerning whether a particular pant has a gusset with a liquid impermeable barrier layer, this Liquid Impermeability test method may be used to measure a quantity of test liquid that will pass through a sample and enable determination whether there is a "liquid impermeable barrier layer" present in the gusset, according to the definition set forth in the description above.

The Liquid Impermeability test measures the quantity of liquid transferred through to the outward-facing side of a test specimen obtained from a pant after it is dosed with a prescribed volume of test liquid in order to simulate a liquid insult during actual use/wear of the pant.

All testing is performed in a room controlled at 23° C.±3C° and 50%±2% relative humidity.

Prior to performing the measurement of this method, the examples of the pants of interest (prior to removal of samples therefrom) are washed in order to mimic in-use conditions and to follow the recommended "prior to use" instructions that accompany these types of pants (e.g. wash before use). The examples are placed into a mesh lingerie bag, and then placed into a high efficiency, front-loading washing machine (any convenient source) along with a single small/light load dosage of TIDE brand laundry detergent ("Original" designation; "HE" or other high efficiency washing machine designation; without additives such as FEBREZE, ODOR DEFENSE, OXI additives, bleach or bleaching additives or fabric softening additives) (product of The Procter & Gamble Company, Cincinnati, Ohio), or equivalent. The washer is set to delicate cycle using cold water. After the wash cycle, the examples are removed from the mesh bag and placed flat on a drying rack to air dry for about 12 hours. After air-drying, the examples are placed into a clothes dryer (any convenient source) set on the delicate cycle with very low heat for about 5 minutes or until dry to the touch.

Test samples are prepared as follows. The pre-washed and dried example pants are equilibrated in a room controlled at 23° C.±3C° and 50%±2% relative humidity for about 2 hours. Test samples containing the entire gusset are removed from the examples as described in the General Sample Preparation section herein. Using scissors, the outermost fabric layer on the outward-facing side of the gusset is cut out along the entire gusset shape, inboard of the seams, using care so as not to cut into any of the edge seams present. Mark the dose location at the intersection of the midpoint of the longitudinal axis of the sample and a lateral axis positioned at the narrowest portion of the specimen.

For each test sample, a single layer of filter paper is cut to 10 cm by 2.54 cm. A suitable filter paper is Ahlstrom Grade 989 (available from Ahlstrom-Munksjo North America LLC, Alpharetta, GA), or equivalent. The test liquid is deionized water at room temperature (23° C.±) 3C°.

Record the mass of one layer of pre-cut filter paper and record as Dry Massip to the nearest 0.0001 grams. Place the pre-weighed filter paper onto a flat horizontal work surface. Position the test specimen centered over the filter paper with the garment facing side of the specimen facing the paper. Using a volumetric pipette, apply a 1.0 ml dose of test liquid to the pre-marked dosing location as follows. The tip of the pipette is held about 3 mm above the surface of the test specimen, and the dose is applied slowly (about 30 seconds) to avoid splashing. As soon as the entire dose has been applied, start a 1 minute timer. After 1 minute has elapsed, remove the test specimen and record the mass of the filter paper as Wet Massip to the nearest 0.0001 grams. Subtract the Dry Massfp from the Wet Massfp and record as z-Direction Leakage to the nearest 0.0001 grams.

In like fashion, repeat for a total of three replicate test specimens. Calculate the arithmetic mean for z-Direction Leakage and report to the nearest 0.0001 g.

Ordinary X-Y Plane Dimensions

For purposes herein, when a length or width of a feature of a pant is specified, it is to be measured with the pant laid out flat on a horizontal planar surface (in an opened or assembled configuration, as appropriate) with the material of the pant smoothed out flat, but in a relaxed condition, not pulled or stretched along any planar direction.

In view of the foregoing description, the following examples are contemplated, although the identification thereof is not intended to be limiting:

1. A durable absorbent pant, comprising:
   a front waist portion (100) with a front waist edge (102) and left and right front leg opening edges (104);
   a rear waist portion (120) with a rear waist edge (122) and left and right rear leg opening edges (124);
   a crotch portion (130) comprising a crotch gusset (230), the crotch portion having a forward portion (132) meeting the front waist portion and a rearward portion (136) meeting the rear waist portion; and
   left and right hip side portions (160) joining the front waist portion to the rear waist portion and thereby forming a waist opening with a waist opening edge comprising the front waist edge (102) and the rear waist edge (122), and left and right leg openings;
   wherein, when the pant is in an opened configuration in which the front waist portion and rear waist portion are separated at the hip side portions, the pant has a longitudinal axis (200) and a lateral axis (300), with an intersection (250) thereof, the intersection occurring in the crotch portion (130);
   wherein each of the front waist portion (100), rear waist portion (120) and crotch gusset (230) comprises a knitted material; and
   wherein the crotch gusset (230) comprises an absorbent assembly (131) comprising an absorbent layer (131b) and a liquid impermeable barrier layer disposed to the outward-facing side of the absorbent layer, and exhibits a maximum Longitudinal Elongation of 25 percent to 100 percent and a Longitudinal Tensile Modulus of 10 gf/mm to 100 gf/mm; and
   the crotch portion has a central Caliper at the intersection (250) of the lateral and longitudinal axes.

2. The pant of example 1 wherein the crotch gusset exhibits a Volume Absorption Capacity of at least 0.50 ml/cm$^3$, up to 1.2 ml/cm$^3$.

3. The pant of either of examples 1 or 2, wherein the pant is a brief pant and has a minimum crotch width CW of at least 8 cm.

4. The pant of any of the preceding examples wherein the absorbent assembly comprises a plurality of layer components.

5. The pant of example 4 wherein at least one of the layer components comprises an elastic material.

6. The pant of example 5 wherein the elastic material comprises elastic fiber, thread or yarn.

7. The pant of example 5 wherein the elastic material comprises an elastic film.

8. The pant of either of examples 6 or 7 wherein the elastic material comprises a material selected from the group consisting of PET, TPEE, elastane and polyurethane, and combinations thereof.

9. The pant of any of the preceding examples wherein the absorbent assembly comprises a wearer-facing layer (131a) comprising a first knitted fabric material.

10. The pant of example 9 wherein the first knitted fabric material is knitted of one or more yarns that comprise synthetic material selected from the group consisting of polyester, polyamide, polypropylene, polyethylene and combinations thereof.

11. The pant of any of the preceding examples wherein the absorbent assembly comprises an absorbent layer (131b) comprising a second knitted fabric material.

12. The pant of example 11 wherein the second knitted fabric material is a knitted terrycloth material.

13. The pant of either of examples 11 or 12 wherein the second knitted fabric material is knitted of one or more yarns that comprise material selected from the group consisting of cotton, rayon, viscose, polyester, polyamide and combinations thereof.

14. The pant of any of examples 11-13 wherein the second knitted fabric material comprises a microfiber yarn.

15. The pant of any of examples 11-14 wherein the first knitted fabric material and/or the second knitted fabric material comprises an antimicrobial agent selected from the group consisting of carbon; a metal or alloy or compound thereof; and combinations thereof.

16. The pant of example 15 wherein the metal is selected from the group consisting of copper, silver, zinc, aluminum and combinations thereof.

17. The pant of any of the preceding examples wherein the Caliper is no greater than 5 mm, more preferably no greater than 4 mm, and even more preferably no greater than 3.5 mm.

18. The pant of any of the preceding examples wherein the crotch portion comprises four layers comprising a wearer-facing layer (131a), an absorbent layer (131b) directly beneath the wearer-facing layer, a liquid impermeable barrier layer (131c) beneath the absorbent layer and an outward-facing layer (131d) beneath the barrier layer.

19. The pant of example 18 wherein any of the wearer-facing layer, absorbent layer and outward-facing layer comprises elastic filaments.

20. The pant of example 19 wherein the barrier layer is a polymeric film.

21. The pant of example 20 wherein the polymeric film has been applied in liquid, semi-molten or molten form to an outward-facing side of a superadjacent knitted fabric and has thereby partially penetrated texture of the outward-facing side thereof.

22. The pant of either of examples 20 or 21 wherein the polymeric film is an elastomeric film.

23. The pant of any of examples 20-22 wherein the polymeric film comprises a material selected from the group consisting of PET, TPEE, elastane and polyurethane, and combinations thereof.

24. The pant of any of the preceding examples wherein a wearer-facing layer is thermal compression bonded to an underlying absorbent layer in a pattern of thermal compression bonds.

25. The pant of any of the preceding examples, wherein the crotch portion has a perimeter and comprises a perimeter containment barrier (170) disposed along and proximate to at least a portion of the perimeter on the wearer-facing side of the crotch portion, the crotch portion at a containment barrier location having a z-direction containment barrier Caliper that is greater than the central Caliper; and
   wherein the containment barrier comprises a hydrophobic material and forms a laterally inward-facing surface that is hydrophobic.

26. The pant of example 25 wherein the containment barrier comprises a foam material.

27. The pant of either of examples 25 or 26 wherein the containment barrier together with the underlying material of the crotch portion is elastically extensible.

28. The pant of any of examples 25-27 wherein at least portions of the containment barrier are curved in an x-y plane.

29. The pant of example 28 wherein the curvature follows curvature of the leg opening edges.

30. The pant of any of examples 25-29 wherein the containment barrier comprises a bead of containment barrier material applied to the crotch portion in liquid, semi-molten or molten form to a wearer-facing surface of the crotch portion.

31. The pant of example 30 wherein the containment barrier material comprises silicone.

32. The pant of either of examples 30 or 31 wherein the containment barrier comprises flocking applied to the surface of the bead of containment barrier material.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A durable absorbent pant, comprising:
   a front waist portion with a front waist edge and left and right front leg opening edges;
   a rear waist portion with a rear waist edge and left and right rear leg opening edges;
   a crotch portion comprising a crotch gusset, the crotch portion having a forward portion meeting the front waist portion and a rearward portion meeting the rear waist portion; and
   left and right hip side portions joining the front waist portion to the rear waist portion and thereby forming a waist opening with a waist opening edge comprising the front waist edge and the rear waist edge, and left and right leg openings;
   wherein, when the pant is in an opened configuration in which the front waist portion and rear waist portion are separated at the hip side portions, the pant has a longitudinal axis and a lateral axis, with an intersection thereof, the intersection occurring in the crotch portion;
   wherein each of the front waist portion, rear waist portion and crotch gusset comprises a knitted material;
   wherein the crotch gusset comprises an absorbent assembly comprising a wearer-facing layer comprising a knitted fabric material, an absorbent layer comprising knitted terrycloth material, and a liquid impermeable barrier layer disposed to the outward-facing side of the absorbent layer, and wherein the crotch gusset exhibits a maximum Longitudinal Elongation of 25 percent to 100 percent and a Longitudinal Tensile Modulus of 10 gf/mm to 100 gf/mm and a Volume Absorption Capacity of at least 0.50 ml/cm$^3$, up to 1.2 ml/cm$^3$;
   wherein the crotch portion has a central Caliper at the intersection of the lateral and longitudinal axes; and
   wherein the crotch gusset is joined to the front waist portion at a first seam and the rear waist portion at a second seam, wherein the first and second seams comprising one or more of stitching, adhesive bonding or thermal bonding.

2. The pant of claim 1, wherein the pant is a brief pant and has a minimum crotch width CW of at least 8 cm.

3. The pant of claim 1, wherein the absorbent assembly comprises a plurality of layer components, and at least one of the layer components comprises an elastic material.

4. The pant of claim 3, wherein the elastic material comprises one or more of elastic fiber, elastic thread, elastic yarn or elastic film.

5. The pant of claim 3, wherein the elastic material comprises a material selected from the group consisting of PET, TPEE, elastane and polyurethane, and combinations thereof.

6. The pant of claim 1, wherein the knitted fabric material is knitted of one or more yarns that comprise synthetic material selected from the group consisting of polyester, polyamide, polypropylene, polyethylene and combinations thereof.

7. The pant of claim 1, wherein the absorbent knitted fabric material is knitted of one or more yarns that comprise material selected from the group consisting of cotton, rayon, viscose, polyester, polyamide and combinations thereof.

8. The pant of claim 1, wherein the absorbent knitted fabric material comprises a microfiber yarn.

9. The pant of claim 1, wherein the Caliper is no greater than 5 mm.

10. The pant of claim 1, wherein the crotch portion comprises four layers comprising a wearer-facing layer, an absorbent layer directly beneath the wearer-facing layer, a liquid impermeable barrier layer beneath the absorbent layer and an outward-facing layer beneath the barrier layer.

11. The pant of claim 10, wherein any of the wearer-facing layer, absorbent layer and outward-facing layer comprises elastic filaments.

12. The pant of claim 10, wherein the barrier layer is a polymeric film.

13. The pant of claim 12, wherein the polymeric film has been applied in liquid, semi-molten or molten form to an outward-facing side of a superadjacent knitted fabric and has thereby partially penetrated texture of the outward-facing side thereof.

14. The pant of claim 12, wherein the polymeric film is an elastomeric film.

15. The pant of claim 12, wherein the polymeric film comprises a material selected from the group consisting of PET, TPEE, elastane and polyurethane, and combinations thereof.

16. The pant of claim 1, wherein the wearer-facing layer is thermal compression bonded to the absorbent layer in a pattern of thermal compression bonds.

17. The pant of claim 1, wherein the crotch gusset comprises inside leg opening edges, and wherein the wearer-facing layer, the absorbent layer, and the liquid impermeable barrier layer are joined at the inside leg opening edges.

* * * * *